US010660740B2

(12) United States Patent
Prandi et al.

(10) Patent No.: US 10,660,740 B2
(45) Date of Patent: May 26, 2020

(54) IMPLANTABLE FASTENING DEVICE FOR SECURING A GRAFT TO AT LEAST ONE BONE OF A JOINT

(71) Applicant: COUSIN BIOTECH, Wervicq Sud (FR)

(72) Inventors: Jules Prandi, Tourcoing (FR); Farid Kamche, Tourcoing (FR)

(73) Assignee: COUSIN BIOTECH, Wervicq Sud (FR)

( * ) Notice: Subject to any disclaimer, the term of this patent is extended or adjusted under 35 U.S.C. 154(b) by 91 days.

(21) Appl. No.: 15/818,874

(22) Filed: Nov. 21, 2017

(65) Prior Publication Data
US 2018/0140416 A1 May 24, 2018

(30) Foreign Application Priority Data
Nov. 21, 2016 (FR) ...................................... 16 61308

(51) Int. Cl.
*A61F 2/08* (2006.01)
*A61B 17/06* (2006.01)
*A61B 17/04* (2006.01)

(52) U.S. Cl.
CPC ........ *A61F 2/0811* (2013.01); *A61B 17/0401* (2013.01); *A61B 17/06166* (2013.01);
(Continued)

(58) Field of Classification Search
CPC .. A61F 2/0811; A61F 2/08; A61F 2002/0852; A61B 2017/06185;
(Continued)

(56) References Cited

U.S. PATENT DOCUMENTS 9,168,118 B2   10/2015  Noel et al.
2017/0333038 A1*  11/2017  Hallett ..................... D04C 1/06

FOREIGN PATENT DOCUMENTS

| FR | 2980356 A1 | 3/2013 | |
| FR | 2980356 B1 * | 10/2013 | ......... A61B 17/0487 |
| WO | 2012/154922 A2 | 5/2012 | |

OTHER PUBLICATIONS

Debbabi F, et al "Tensile Behaviour of Polyester Braided Suture" Conference Paper, International Conference of Applied Research in Textiles, Jan. 2013. (Year: 2013).*
(Continued)

*Primary Examiner* — Brian A Dukert
*Assistant Examiner* — Rebecca Lynee Zimmerman
(74) *Attorney, Agent, or Firm* — MH2 Technology Law Group, LLP

(57) ABSTRACT

The present disclosure provides an implantable fastening device for securing a graft to at least one bone of a joint, comprising a hollow tubular elongate textile element defining an inside volume and including a first free end and a second free end; and a bearing element having at least two through openings. Said elongate element has an initial outside diameter d0 (mm) and includes an admission orifice leading into its inside volume and an exit orifice going from its inside volume that are spaced apart by an initial distance m0 (mm) defining a sleeve, the first end of said elongate element being passed into the sleeve so as to form a first loop with at least a portion thereof being passed through at least two through openings of said bearing element. The second free end of said elongate element forms a second loop passing through a through opening of said bearing element. The sleeve receiving a portion of elongate element has an outside diameter at rest n0, and the distance m0 and the outside diameter d0 of said elongate element are determined in such a manner that in operation, traction exerted on the
(Continued)

first free end causes the admission and exit orifices to move towards each other and correspondingly causes the sleeve to expand radially.

16 Claims, 5 Drawing Sheets

(52) U.S. Cl.
CPC ........... *A61B 2017/0404* (2013.01); *A61B 2017/06185* (2013.01); *A61F 2002/0817* (2013.01); *A61F 2002/0852* (2013.01); *A61F 2002/0882* (2013.01); *A61F 2210/0014* (2013.01)

(58) Field of Classification Search
CPC ............ A61B 2017/0404; A61B 17/04; A61B 17/0487; A61B 17/0401; A61B 17/06166
See application file for complete search history.

(56) References Cited

OTHER PUBLICATIONS

Translation of FR2980356 (Year: 2013).*

* cited by examiner

IMPLANTABLE FASTENING DEVICE FOR SECURING A GRAFT TO AT LEAST ONE BONE OF A JOINT

TECHNICAL FIELD

The present disclosure relates to the technical field of implantable fastening devices for securing a graft to at least one bone of a joint, in particular at least one bone of the knee joint in order to reconstruct the anterior or posterior cruciate ligament.

BACKGROUND

Implantable fastening devices for reconstructing the anterior cruciate ligament (ALC) or the posterior cruciate ligament (PCL) make use of a graft that is made to measure. The graft is generally made using the "internal rectus" (RI) tendon or "gracilis" tendon, and the semi tendonius (ST) tendon. The operating technique associated with preparing this graft may be referred to as the "IRST" technique.

The operating technique that consists in using only the semi tendonius tendon folded in four may be referred to as the "ST4" technique.

The operating technique using the central portion of the ligamental patellae is referred to as the "Kenneth Jones" or "KJ" technique for the surgeon who developed it.

All of those surgical treatment methods comprise placing a graft constituted by one or more tendons under arthroscopic monitoring in a tunnel in bone made by drilling into the head of the femur or of the tibia.

The "internal rectus" and the "semi tendonius" muscles are two similar muscles, which together with a third muscle, namely the "sartorius" muscle, form the "pes anserinus". They are also referred to as the "hamstring" muscles and they are located on the medial portion of the thigh. The tendons at this position of the thigh are very long and they are attached to the medial face of the tibia after crossing the knee. It is possible to take these tendons via a small incision of a few centimeters using an instrument of the "stripper" type, which detaches them over their entire length.

Once the tendons have been taken, they are joined together and folded in half, thereby making it possible to form a new ligament referred to as a graft or an autograft that comprises four strands having traction strength that is thus greater than that of a normal anterior cruciate ligament (ACL).

The tunnels drilled in the femur and the tibia enable the graft to be passed inside the joint so as to place it at the location where the anterior cruciate ligament used to be situated. The tunnels in the femur and the tibia open out at the location for the natural attachments of the ligaments. The positioning of these tunnels in the tibia and the femur is important since it has an influence on the subsequent post-operative stability of the knee. The tunnel in the femur is made directly inside the joint via one of the two orifices of the arthroscope or via the previously-drilled tunnel in the tibia. The tunnel in the femur may also be drilled by using a small incision made in the lateral face of the thigh.

The graft is fastened using medical devices at the ends of the previously-drilled tunnels in the femur and the tibia.

Implantable fastening devices are known that are used in particular in the IRST and ST4 operating techniques, which devices comprise fastening means for fastening the ends of the graft to the joint, said fastening means for example being an interference screw inserted in the wall of the tunnel containing the graft and thus blocking the graft against the wall of the tunnel.

The graft may also be fastened by fastening a textile strip to one or both ends of the graft, the fastening means then being applied directly to the textile strip and not to the graft. Another fastening technique comprises a cage arranged in a tunnel and having an inside bore suitable for co-operating with the screw pitch of a blocking screw, the textile strip being blocked in the cage by the screwed-in blocking screw.

Devices of that type do not enable the position of the graft to be adjusted in the tunnels in the femur and the tibia after it has been put into place without new surgery.

WO 2012/154922 provides an implantable device having a hollow elongate element with at least a portion thereof being passed through two through openings of a bearing button, a first end of the elongate element is passed inside the elongate element in its second end and then leaves over the length thereof so as to form a clamping loop. In operation, the size of the clamping loop is adjusted by exerting traction on the free first end of the elongate element, which first end extends at least in the femoral canal and thus comes into contact with the graft. There is thus a risk of abrading and thereby damaging the graft and of modifying its position in the femoral canal, and possibly also in the tibial canal if the first end also extends in that canal.

FR 2 980 356 provides a device having an elongate element provided in two zones of its length with at least two grommets, each receiving one end of the elongate element so as to form two clamping loops. A portion of the elongate element is passed through two through openings of a bearing button.

In comparison with WO 2012/154922, the two free ends of FR 2 980 356 extend away from the two clamping loops, thereby avoiding the two free ends extending through the femoral canal, and possibly the tibial canal.

Nevertheless, traction exerted on the free ends of the elongate element can only adjust the size of the loops in connection with the graft. The device is not provided with means for locking the graft in its implantation position, since if tension is exerted on the graft through the femoral canal, and possibly through the tibial canal, the strands of the elongate element arranged in the loops slide, with the clamping loops becoming larger and the graft is no longer correctly tensioned, and is moved away from its implantation position.

There thus exists a need for an implantable fastening device for fastening a graft to at least one bone of a joint and that enables the position of the graft to be adjusted in at least one bone canal, in particular the femoral canal and the tibial canal, enabling the graft to be locked in said bone canal, in particular the femoral canal and the tibial canal, in a manner that is removable without new surgery; and means for adjusting the position and the tensioning of the graft, with this being done in removable manner.

There also exists a need for an implantable fastening device that is simple to use and that limits the amount of friction exerted on the graft in order to preserve its mechanical properties.

SUMMARY

The present disclosure mitigates the above-mentioned problems in that it provides an implantable fastening device for securing a graft to at least one bone of a joint, e.g. the tibial bone and/or the femoral bone, in particular for reconstructing the anterior or posterior cruciate ligament of the knee, said fastening device comprising:
- a hollow tubular elongate textile element defining an inside volume and including a first free end and a second free end; and
- a bearing element having a bearing face configured to bear against at least said bone of a joint, said bearing element having at least two through openings.

Said elongate element may have an initial outside diameter d0 (mm) and includes an admission orifice leading into its inside volume and an exit orifice going from its inside volume that are spaced apart by an initial distance m0 (mm) defining a sleeve, the first end of said elongate element being passed through said admission and exit orifices into the sleeve so as to form a first loop of adjustable initial perimeter P1, with at least a portion thereof being passed through at least two through openings of said bearing element. The first free end of said elongate element passes through a through opening of said bearing element, and said second free end also passes through a through opening of said bearing element and forms a second loop of adjustable initial perimeter P2. The sleeve receiving a portion of elongate element has an initial outside diameter at rest n0, and the distance m0 and the outside diameter d0 of said elongate element are determined in such a manner that in operation, traction exerted on the first free end causes the admission and exit orifices to move towards each other and correspondingly causes the sleeve to expand radially.

The implantable device of the disclosure thus forms two loops of adjustable perimeter, each suitable for receiving a loop of a ligament and/or a tendon.

The radial expansion of the sleeve may give rise to a diameter n1 (in the compressed state) that is greater than the initial diameter n0 of the sleeve, thereby enabling the implantable device to be fixed in said at least one bone canal in which the device is arranged. The distance m0 and the outside diameter d0 of the elongate element are determined relative to each other in such a manner that the traction exerted on the first free end of the elongate element generates friction between the outer surface of the elongate element and the inside surface of the sleeve, thereby causing it to be compressed radially and thus causing the admission and exit orifices to move towards each other. The distance m1 between the admission and exit orifices of the sleeve in its compressed state is shorter than the initial distance m0 between said admission and exit orifices of the sleeve.

The traction on the first free end of said elongate element may make it possible likewise to adjust the perimeter of the first loop by sliding the elongate element in the sleeve in the compressed state and through the through openings in said bearing element. The initial perimeter P1 of the first loop is thus reduced when traction is exerted on the first free end of the elongate element, thus enabling the position of the tendon or of the ligament to be adjusted in said at least one bone canal.

It is possible to put the sleeve back into its initial state, i.e. its non-compressed state in which the distance between the admission and exit orifices is m0, by exerting traction on the elongate element in a direction opposite to the traction applied for causing compression of the sleeve and by holding the sleeve so that it does not lengthen. The implantable device thus comprises means for fixing and adjusting the position of the graft passed through the first and second loops, which means are removable, for example.

In some embodiments, the distance m0 of the sleeve is greater than or equal to five times, for example, greater than or equal to ten times, possibly greater than or equal to twelve times, and even possibly greater than or equal to fifteen times the outside diameter d0 of the elongate element.

The diameters and the distances on the device according to embodiments of the disclosure such as the distances m0, m1, or m2, can be measured using a caliper, or indeed using a graduated support and a magnifying glass. Distances and diameters are specified in millimeters (mm) in the context of the present disclosure.

In an embodiment, the distance m0 is greater than or equal to 25 mm and less than or equal to 50 mm, for example, greater than or equal to 30 mm and less than or equal to 45 mm.

According to some embodiments, the initial outside diameter m0 of the sleeve (initial state) may be greater than or equal to 1.50 mm and less than or equal to 3 mm, for example, greater than or equal to 2.00 mm and less than or equal to 2.80 mm, possibly being about 2.50 mm.

In some embodiments, the distance m1 may be greater than or equal to 15 mm and less than or equal to 35 mm, for example, greater than or equal to 20 mm, and less than or equal to 35 mm.

The outside diameter n1 of the sleeve (in the compressed state) may be greater than or equal to 1.5 mm and less than or equal to 4 mm, for example, greater than or equal to 2 mm and less than or equal to 3.5 mm.

The outside diameter d0 of the tubular elongate element may be greater than or equal to 1.30 mm and less than or equal to 3 mm, for example, greater than or equal to 1.50 mm and less than or equal to 2.50 mm.

In some embodiments, said at least one portion of elongate element may pass through a first through opening and a second through opening of the bearing element, and the first free end of the elongate element may pass through said first through opening, while the second free end may pass through said second through opening.

The first and second free ends of the elongate element may come out from the bearing element via its outer face opposite from its bearing facing, while the first and second loops may project from the bearing face. This arrangement may make it possible to avoid friction between the first and second free ends of the elongate element and the graft, because said free ends do not extend along said at least one bone canal, and therefore may not slide against and abrade the graft.

In some embodiments, the bearing element may be in the form of a button having at least two through openings, with a bearing face suitable for bearing against a bone element and an outer face opposite from its bearing face.

The bearing element may be made of any implantable material, and in particular out of an alloy of titanium and nickel, e.g. nitinol; or indeed out of an alloy of titanium and aluminum, such as the alloy known under the reference Ti 6Al-4V which is a titanium alloy having 6% by weight aluminum and 4% by weight vanadium relative to the total weight of said alloy, the balance being titanium; or indeed a synthetic material, for example, selected from the following synthetic materials:
polyethyleneterephthalate; polyamide 6, polyetheretherketone (PEEK), in particular having the trademark PEEK-OPTIMA®, or indeed the trademark OXPEKK®; and ultra-high molecular weight polyethylene (UHMWPE), e.g. having the trademark GUR®.

The first free end and the second free end of said elongate element may project from the outer face of said bearing element, which may be arranged opposite from the bearing face of said bearing element.

The textile elongate element may be flexible because of its textile structure. The textile elongate element could be made as any kind of textile element: woven, knitted, or braided. In terms of compressing and lengthening the sleeve, it may be desirable that the elongate element comprises a braid.

The textile elongate element may comprise fiber-spun yarns and/or multifilament yarns, and for example, may comprise multifilament yarns.

Said fiber-spun yarns and/or multifilament yarns may be selected from the list comprising: polyolefins, in particular UHMWPE polyethylenes, in particular having the trademark DYNEEMA® or the trademark SPECTRA®, or polypropylene; polytetrafluoroethylene (PTFE); polyamides, in particular polyamide 6 or polyamide 6-6; polyesters, in particular polyethyleneterephthalate.

The fiber-spun yarns and/or the multifilament yarns may be made of one or more non-resorbable materials, such as those mentioned above.

Although the implantable device according to embodiments of the disclosure may be used for reconstructing the anterior or posterior cruciate ligament of the knee, it is not limited to that application.

The implantable device of the disclosure can thus be used in general manner in the field of reinserting tendons or ligaments in the shoulder, the hip, the knee, or indeed the ankle in order to repair ruptures, instabilities, and fractures, such as an acromioclavicular fracture, or for performing tenodesis (fastening a tendon to another tendon or to a bone, in the context of the present disclosure, the tendon is fastened to at least one bone).

In the disclosure, the term "graft" covers any ligament or tendon or other equivalent implantable material, for example it may be an autograft or an allograft.

According to some embodiments, the initial perimeter P2 may be greater than the initial perimeter P1, with the initial perimeter P2, for example, being greater than or equal to 1.5 times the initial perimeter P1.

The initial perimeter P1 may be greater than or equal to 75 mm and less than or equal to 300 mm, for example, greater than or equal to 105 mm and less than or equal to 150 mm.

The initial perimeter P2 may be greater than or equal to 0 mm and less than or equal to 200 mm, for example, greater than or equal to 70 mm and less than or equal to 100 mm.

According to some embodiments, the exit orifice of the sleeve may come into abutment against a through opening of said bearing element when, in operation, traction is exerted on said first free end.

This provision may improve the fixing effect on the implantable device and in particular on the sleeve in the bone canal in which it is arranged.

According to some embodiments, when traction is exerted on the second free end of said elongate element, the admission and exit orifices may move apart so as to reach a distance m2 corresponding to a locked position in which the portion of elongate element placed in said sleeve is blocked, in particular the distance m2 is greater than the initial distance m0 between said admission and exit orifices.

In some embodiments, the distance m2 of the sleeve (in the long state) may be greater than or equal to 30 mm and less than or equal to 50 mm, for example, greater than or equal to 35 mm and less than or equal to 45 mm.

The outside diameter n2 of the sleeve (long state) may be about 2.00 mm.

The traction on the second free end of the elongate element may serve correspondingly to adjust the perimeter of the second loop of the device and thus to adjust the position of the tendon and/or the ligament passed through said second loop, but also serves to block sliding of the elongate element in the sleeve. Specifically, the friction acting between the outer surface of the elongate element and the inside surface of the sleeve in a second direction (opposite to the first traction direction on the first end of the elongate element and enabling the sleeve to be compressed) as is obtained by exerting traction on the second free end of the elongate element, enables the admission orifice and the exit orifice to be moved apart from each other and thus enables the sleeve to be lengthened to a distance m2 greater than the distance m0 (initial state) and than the distance m1 (compressed state).

In a variant, traction on the second free end causes the perimeter P2 of the second loop to decrease.

In a variant, the first loop is arranged at least in part inside the second loop, and the first and second loops extend from the bearing face of said bearing element.

In a variant, the elongate tubular element is a braid.

In a variant, the tubular element is a braid of pearl structure.

In the state of the art, this pearl structure is also known as a diamond structure.

This structure makes it possible to obtain results that are good in terms of friction generated between the outer surface of the elongate element and the inside surface of the sleeve.

In a variant, the elongate tubular element is a braid comprising a first group of braided strands and a second group of braided strands, the first group of strands having Z twist while the second group of strands has S twist.

This provision may be achieved by placing each strand of the first group of strands on a spindle rotating in the Z direction while each strand of the second group of strands is placed on a spindle rotating in the S direction.

The first group of strands may have a number of strands that is of the order of 0.8 to 1.2 times, for example, of the order of 0.9 to 1.1 times the number of strands in the second group of strands. This provision serves to obtain balanced assembly between the first and second groups of strands with good friction between the inside surface of the sleeve and the outer surface of the elongate element.

In a variant, the elongate tubular element is a braid having a first group of strands in which each strand forms an angle $\alpha$ between the longitudinal axis L of the braided elongate tubular element and the transverse axis T that is substantially perpendicular to axis L, which angle $\alpha$ is greater than or equal to $(+)10°$ and less than or equal to $(+)90°$, and a second group of strands in which each strand forms an angle $\beta$ defined between the longitudinal axis L of the braided elongate tubular element and the transverse axis T that is substantially perpendicular to the axis L, which angle $\beta$ is greater than or equal to $(+)100°$ and less than or equal to $(+)180°$.

The term "+" indicates that the angle is measured in the counterclockwise direction.

The Applicant has observed that this provision makes it possible to obtain results that are good in terms of friction between the sleeve and the elongate element and in terms of withstanding rupture.

The elongate element of the disclosure is intended to remain implanted, where it will be subjected to numerous mechanical stress in particular when it is implanted in a joint (traction, shear, bending, . . . ), so it needs to present sufficient breaking strength.

The tubular elongate element of the disclosure has breaking strength greater than or equal to 500 newtons (N), in particular of about 800 N, with elongation at break less than or equal to 15%, and in particular about 5%.

According to some embodiments, the first group of strands, and optionally the second group of strands comprise(s) at least 4 strands, for example, at least 8 strands, possibly at least 12 strands, or even at least 16 strands.

According to some embodiments, each strand of the first group of strands, and optionally of the second group of strands, comprise(s) at least 4 yarns, for example, at least 6 yarns, that are twisted with a number of twists per meter lying in the range 100 to 300.

Said yarn(s) may be fiber-spun yarns and/or multifilament yarns, for example, multifilament yarns as defined above with reference to the tubular elongate element.

According to some embodiments, the textile elongate tubular element comprises yarns having weight greater than or equal to 100 dtex and less than or equal to 300 dtex.

BRIEF DESCRIPTION OF THE DRAWINGS

The present disclosure can be understood on reading the following description of an embodiment of the disclosure, given by way of non-limiting example and shown in the following figures, in which.

DETAILED DESCRIPTION

Figure 1:
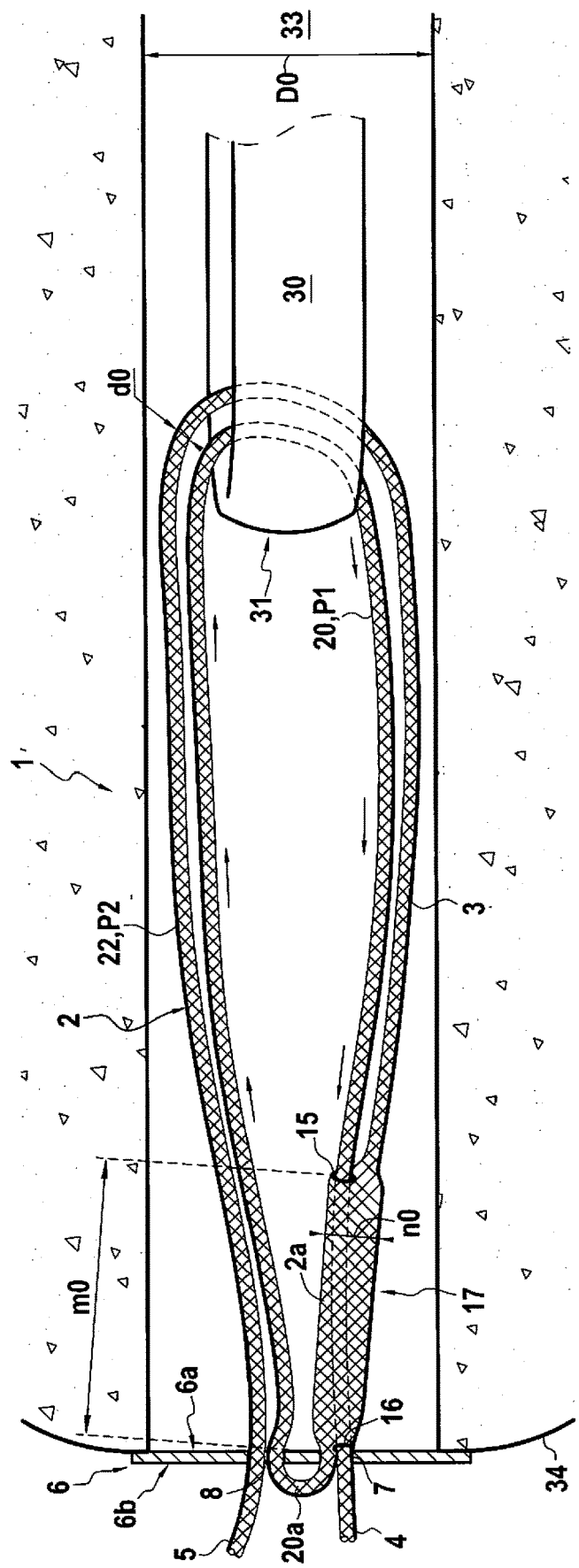
FIG. 1 is a diagrammatic view of an example of an implantable device of the disclosure in its initial state.

The implantable fastening device 1 shown in FIG. 1 may be implemented for securing a graft to at least one bone of a joint, in particular the tibia bone and/or the femur bone in order to reconstruct the anterior or posterior cruciate ligament of the knee. This application is not intended to be limiting for the implantable device 1 described below.

The implantable device 1 comprises a hollow tubular elongate textile element 2 defining an inside volume 3 and having a first free end 4 and a second free end 5, together with a bearing element 6 having a bearing face 6a configured to bear against at least one bone of a joint, said bearing element 6 having at least two through openings, in particular first and second through openings 7 and 8. The bearing element 6 has an outer face 6b opposite from is bearing face 6a. The bearing element 6 comprises, for example, a button.

FIG. 1 shows the elongate element 2 in its initial state. The elongate element 2 in this initial state presents an initial outside diameter d0 (mm), e.g. of the order of 2.30 mm, and has an admission orifice 15 leading to its inside volume and an exit orifice 16 going from its inside volume that are spaced apart by an initial distance m0 (mm) defining a sleeve 17. The first end 4 of said elongate element 2 is passed through said admission and exit orifices 15 and 16 into the sleeve 17 in such a manner as to form a first loop 20 of adjustable initial perimeter P1, having at least a portion 20a that is passed through the first and second through openings 7 and 8 of said bearing element 6. The first free end 4 of said elongate element 2 passes through said first through opening 7 of said bearing element 6, and said second free end 5 of the elongate element 2 passes through the second through opening 8 of said bearing element 6 and forms a second loop 22 of adjustable initial perimeter P2. The sleeve 17 receiving said portion 2a of the elongate element 2 has a rest outside diameter n0. In this particular example, n0 is of the order of 2.50 mm.

The distance m0 and the outside diameter d0 of said elongate element 2 are determined in such a manner that in operation, traction exerted on the first free end 4 causes the admission and exit orifices 15 and 16 to move towards each other, and correspondingly causes the sleeve 17 to expand radially.

The distance m0 (mm) is greater than ten times the outside diameter d0 of the elongate element 2. In this specific example, the distance m0 is about 40 mm.

The initial perimeter P2 of the second loop 22 is greater than the initial perimeter P1, and the initial perimeter P2 may be greater than or equal to 1.5 times the initial perimeter P1.

In operation, with the exit orifice 16 of the sleeve 17 arranged directly facing the first through opening 7 of the bearing element 6, the exit orifice 16 of the sleeve 17 comes into abutment against the first through opening 7.

As shown in the figures, the first loop 20 is arranged inside the second loop 22, and the first and second loops 20 and 22 extend from the bearing face 6a of said bearing element 6.

Figure 4:
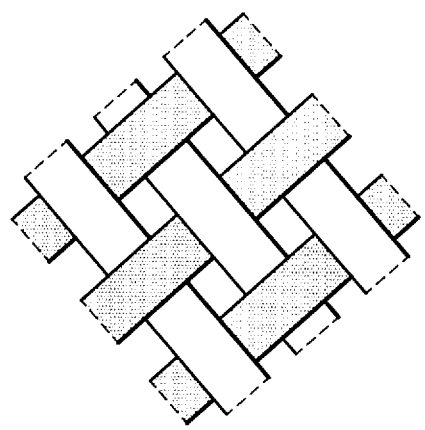
FIG. 4 is a diagram showing the pearl or diamond braiding pattern used for the elongate element of the implantable device shown in FIGS. 1 to 3.

The elongate tubular element 2 is a hollow tubular braid of pearl structure (also referred to as being of "diamond" structure), as shown in FIG. 4, which is obtained by knitting a first group of braided strands 25 and a second group of braided strands 26, the first group of strands 25 having a Z twist while the second group of strands 26 has an S twist. On the braiding machine, each strand is supported individually on a spindle.

Figure 5:
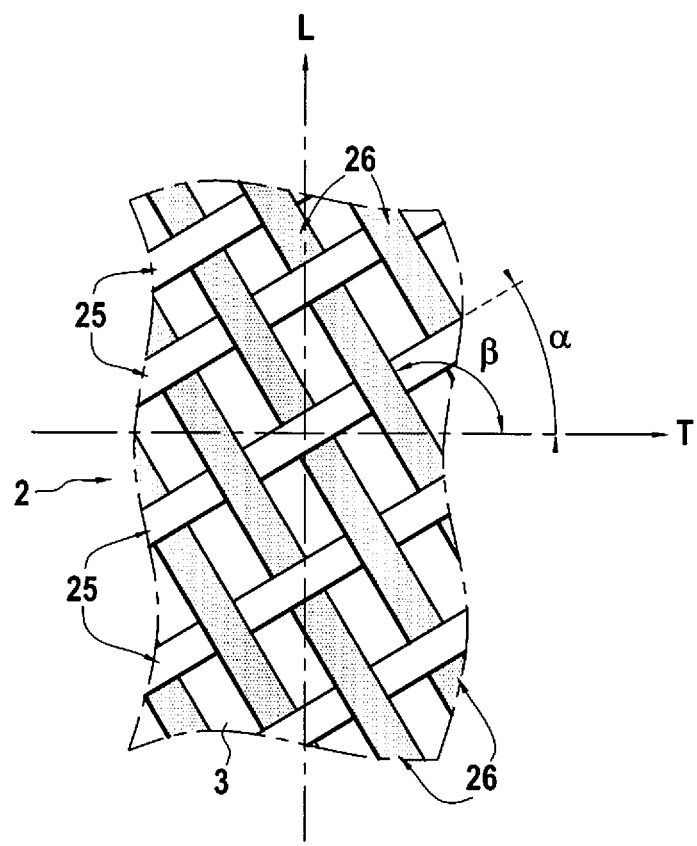
FIG. 5 is a diagram showing the angle formed between the first and second groups of braided strands forming the elongate element of the implantable device shown in FIGS. 1 to 3.

Each strand of the first group of strands 25 forms an angle α between the longitudinal axis L of the braided elongate tubular element 2 and the transverse axis T that is substantially perpendicular to the axis L, which angle α is greater than or equal to +10° C. and less than or equal to +90°, as shown in FIG. 5. In parallel, each strand of the second group of strands 26 forms an angle β between the longitudinal axis L of the braided elongate tubular element 2 and the transverse axis T, which angle β is greater than or equal to +100° C., and less than or equal to +180° C., likewise shown in FIG. 5.

The first group of strands 25 and the second group of strands 26 comprise eight strands each. Each strand (whether of the first group 25 or of the second group 26) comprises six multifilament yarns, each of 138 dtex, that are twisted at about 200 twists per meter.

Figure 2:
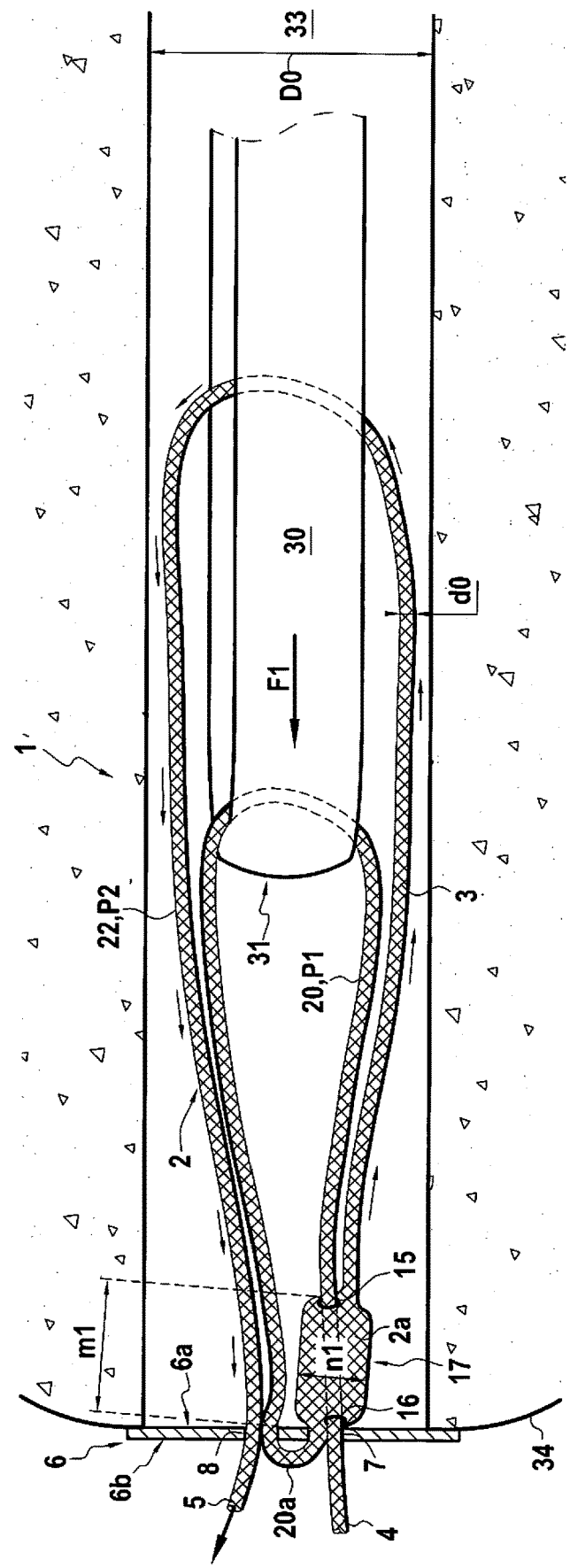
FIG. 2 is a diagrammatic view of the example implantable device shown in FIG. 1 in which the sleeve is in its compressed state corresponding to a fixed position of the device.
Figure 3:
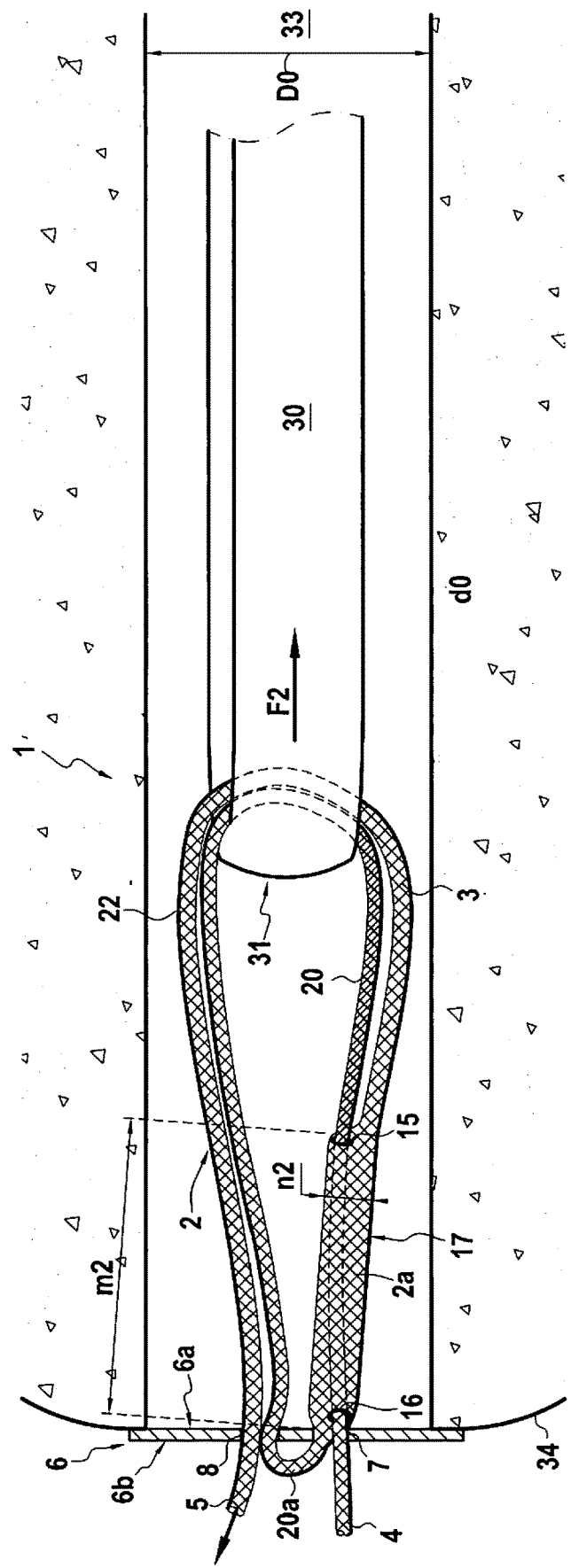
FIG. 3 is a diagram showing the example implantable device shown in FIGS. 1 and 2, in which the sleeve is in its long state corresponding to a locked position of said device.

In operation, the surgeon prepares the graft 30 so as to form a loop 31 therein and passes this loop 31 through the first and second loops 20 and 22 of the implantable device 1, and then places the implantable device 1 secured to the graft 30 in at least one bone canal 33 having a main section of constant inside diameter D0. Only one bone canal 33 is shown in FIGS. 1 to 3, however the graft 30 could be passed through two bone canals, such as the tibial canal and the femoral canal. Only the loop 31 of the graft 30 is shown in FIGS. 1 to 3, however the free end (not shown) of the graft 30 may be fastened to the bone wall by any means known in the state of the art, such as for example using a hollow implant housed in said at least one bone canal 33 and receiving said end, which is blocked by means of a screw screwed into the hollow implant.

Once the graft 30 has passed into said at least one bone canal 33, with the bearing face 6a of the bearing element 6 bearing against a bone wall 34, and with the first and second free ends 4 and 5 of the elongate element 2 projecting from the outer face 6b of said bearing element 6, opposite from the bearing face 6a, the surgeon exerts traction on the first free end 4 of the elongate element 2 in a direction F1, thereby causing the perimeter P1 of the first group 20 to decrease, the admission and exit orifices 15 and 16 of the sleeve 17 to move towards each other, and correspondingly the sleeve 17 to expand radially so as to adopt an outside diameter n1 of about 3 mm, the distance m1 being of the order of 30 mm. These various technical effects enable the position of the graft 30 in said at least one bone canal 33 to be adjusted, thereby assisting in tensioning it correctly, and enabling the sleeve 17 to be fixed in said at least one bone canal 33, thus preventing any unwanted movement of the elongate element 2 and thus correspondingly of the graft 30.

Fixing of the implantable device 1 is further improved by the friction exerted by the exit orifice 16 of the sleeve 16 coming into abutment against the first through opening 7 of the bearing element 6.

Thereafter, the surgeon extracts traction on the second free end 5 of the elongate element 2, causing the sleeve 17 to extend in the direction F2, opposite to the direction F1, and thus away from the admission and exit orifices 15 and 16 of the sleeve 17. The sleeve 17 then presents a distance m2 that is greater than the distance m0 or m1, and an outside diameter n2 that is less than the diameters n0 and n1. In this particular example, the distance m2 is about 50 mm and the diameter n2 is about 2 mm. This lengthened position of the sleeve 17 serves to block sliding of the elongate element 2 in said sleeve 17 and thus to lock the elongate element 2 in this position, thereby blocking the position of the graft 30 in said at least one bone canal 33. Traction on the second free end 5 also serves to reduce the perimeter P2 of the second loop 22, and optionally once more adjust the position of the graft 30 in said at least one bone canal 33.

The implantable device 1 of the disclosure enables the elongate element 2 to be fixed and blocked in a manner that is reversible, since it suffices to exert traction on the first free end 4 or on the second free end 5 in a direction opposite to the direction F1 or F2, while holding the sleeve 17 so as to release the elongate element 2 and enable it once more to slide in the sleeve 17.

The implantable device 1 of the disclosure thus may make it possible to fix the graft 30, then to adjust its position in at least the bone canal 33, and finally to block the graft in its implantation position, and to do so in a manner that is reversible without damaging tissues, the bone canal, or the graft during any of the steps performed by the implantable device 1.

Figure 6:
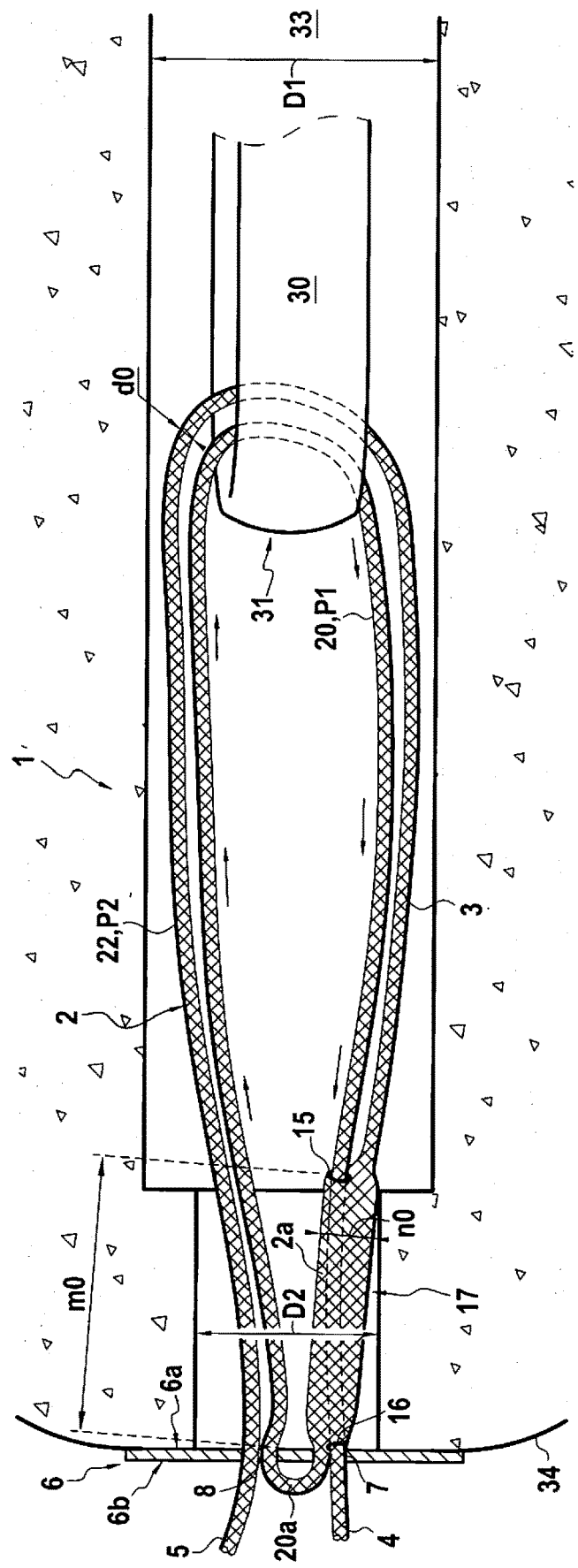
FIG. 6 is a diagram showing the FIG. 1 device in which the anatomical canal is of a morphology that is different from that shown in FIG. 1.

The implantable device 1 is shown in FIG. 6 in a bone canal that presents two sections having two different inside diameters, respectively a first section of inside diameter D2 opening out at the bearing element 6 and receiving the sleeve 17, and a second section of inside diameter D1 receiving the graft 30 passed through the first and second loops 20 and 22. Under such circumstances, when the sleeve 17 is in the compressed state, the fixing of the sleeve 17 in the smaller diameter D2 section of the bone canal is facilitated and improved in comparison with the bone canal shown in FIGS. 1 to 3 having only one section of inside diameter D0.

Throughout the description, including the claims, the term "comprising a" should be understood as being synonymous with "comprising at least one" unless otherwise stated. In addition, any range set forth in the description, including the claims should be understood as including its end value(s) unless otherwise stated. Specific values for described elements should be understood to be within accepted manufacturing or industry tolerances known to one of skill in the art, and any use of the terms "substantially" and/or "approximately" and/or "generally" should be understood to mean falling within such accepted tolerances.

Although the present disclosure herein has been described with reference to particular embodiments, it is to be understood that these embodiments are merely illustrative of the principles and applications of the present disclosure.

The invention claimed is:

1. An implantable fastening device for securing a graft to at least one bone of a joint, said fastening device comprising:
    a hollow tubular elongate textile element defining an inside volume and including a first free end and a second free end; and
    a bearing element having a bearing face configured to bear against at least said bone of a joint, said bearing element having at least two through openings,
    wherein said hollow tubular elongate textile element has an initial outside diameter and includes an admission orifice leading into its inside volume and an exit orifice going from its inside volume that are spaced apart by an initial rest distance (m0) defining a sleeve, the first end of said hollow tubular elongate textile element being passed through said admission and exit orifices into the sleeve so as to form a first loop of adjustable initial perimeter (P1), with at least a portion thereof being passed through at least two through openings of said bearing element, wherein the first free end of said hollow tubular elongate textile element passes through a through opening of said bearing element, wherein said second free end passes through a through opening of said bearing element and forms a second loop of adjustable initial perimeter (P2), wherein the sleeve receiving a portion of the hollow tubular elongate textile element has an outside diameter at rest (n0), and wherein the distance (m0) and the outside diameter (d0) of said hollow tubular elongate textile element are determined in such a manner that in operation, traction exerted on the first free end causes the admission and exit orifices to move towards each other and correspondingly causes the sleeve to expand radially in a compressed state in which a distance between the admission orifice and the exit orifice of the sleeve is (m1), with (m1) being shorter than (m0); and
    wherein when traction is exerted on the second free end of said hollow tubular elongate textile element, the admission and exit orifices of said sleeve moving apart to reach a distance (m2) corresponding to a locked position in which the portion of the hollow tubular elongate textile element placed in said sleeve is blocked.

2. The fastening device according to claim 1, wherein the initial perimeter (P2) is greater than the initial perimeter (P1).

3. The fastening device according to claim 1, wherein the exit orifice of the sleeve comes into abutment against a through opening of said bearing element when, in operation, traction is exerted on said first free end.

4. The fastening device according to claim 1, wherein traction on the second free end causes the perimeter (P2) of the second loop to decrease.

5. The fastening device according to claim 1, wherein the first loop is arranged, at least in part, inside the second loop, and in that the first and second loops extend from the bearing face of said bearing element.

6. The fastening device according to claim 1, wherein the hollow elongate tubular textile element is a braid.

7. The fastening device according to claim 1, wherein the hollow elongate tubular textile element is a braid of pearl structure.

8. The fastening device according to claim 1, wherein the hollow elongate tubular textile element is a braid comprising a first group of braided strands and a second group of braided strands, the first group of strands having Z twist while the second group of strands has S twist.

9. The fastening device according to claim 1, wherein the hollow elongate tubular textile element is a braid having a first group of strands in which each strand forms an angle $\alpha$ between the longitudinal axis (L) of the braid and the transverse axis (T) that is perpendicular to axis (L), which angle $\alpha$ is greater than or equal to 10° and less than or equal to 90°, and a second group of strands in which each strand forms an angle $\beta$ defined between the longitudinal axis (L) of the braid and the transverse axis (T) that is perpendicular to the axis (L), which angle $\beta$ is greater than or equal to 100° and less than or equal to 180°.

10. The fastening device according to claim 8, wherein the first group of strands comprises at least four strands.

11. The fastening device according to claim 8, wherein the second group of strands comprises at least four strands.

12. The fastening device according to claim 8, wherein the first and second group of strands each comprises between four and sixteen strands.

13. The fastening device according to claim 8, wherein each strand of the first group of strands, comprise at least four yarns, that are twisted with a number of twists per meter lying in the range 100 to 300.

14. The fastening device according to claim 1, wherein the hollow tubular elongate textile element comprises yarns having weight greater than or equal to 100 dtex and less than or equal to 300 dtex.

15. The fastening device according to claim 10, wherein the first group of strands comprises at least one of: eight strands, twelve strands, and sixteen strands.

16. The fastening device according to claim 11, wherein the second group of strands comprises at least one of: eight strands, twelve strands, and sixteen strands.

* * * * *